| United States Patent [19] | [11] Patent Number: 4,853,334 |
|---|---|
| Vandenbergh et al. | [45] Date of Patent: Aug. 1, 1989 |

[54] METHOD FOR THE DEGRADATION OF VOLATILE CHLORINATED ALIPHATIC HYDROCARBONS USING PSEUDOMONAS FLUORESCENS

[75] Inventors: Peter A. Vandenbergh, Sarasota; Blair S. Kunka, Bradenton, both of Fla.

[73] Assignee: Microlife Technics, Inc., Sarasota, Fla.

[21] Appl. No.: 186,962

[22] Filed: Apr. 27, 1988

[51] Int. Cl.[4] .................. C07B 63/00; C07C 19/00
[52] U.S. Cl. .................................. 435/262; 435/264; 210/601
[58] Field of Search ................. 435/262, 264; 210/601

[56] References Cited

U.S. PATENT DOCUMENTS 4,259,444  3/1981  Chakrabarty .................. 435/264

OTHER PUBLICATIONS

Koltai et al–Chem. Abst., vol. 97, (1982), p. 54793g.
Nelson, M. J., et al., Appl. Environ. Microbiol., 52:383–384, (1986).
Nelson, M. J., et al., Appl. Environ. Microbiol., 53:949–954, (1987).
Strotmann, U., et al., Curr. Microbiol., 15:159–163, (1987).
Bouwer, E. J., Appl. Environ. Microbiol., 45:1286–1294, (1983).
Vogel, T. M., et al., Environ. Sci. Technol., 21:722–736, (1987).
Stanier, R. Y., et al., J. Gen. Microbiol., 43:159–271, (1966).
Vandenbergh, P. A., et al., Appl. Environ. Microbiol., 42:737–739, (1981).

*Primary Examiner*—Sam Rosen
*Attorney, Agent, or Firm*—Ian C. McLeod

[57] ABSTRACT

A process for degrading volatile halogenated aliphatic hydrocarbons containing 1 to 3 carbon atoms using *Pseudomonas fluorescens* NRRL-B-18296 is described. The method preferably uses a carbon source, such as glucose or molasses, which stimulates the bacterium to degrade the hydrocarbons and which is readily degraded in the environment so that the halogenated aliphatic hydrocarbon is degraded to carbon dioxide, water and hydrochloric acid so that no toxic residues are produced.

20 Claims, No Drawings

METHOD FOR THE DEGRADATION OF VOLATILE CHLORINATED ALIPHATIC HYDROCARBONS USING PSEUDOMONAS FLUORESCENS

BACKGROUND OF THE INVENTION

(1) Field of the Invention

The present invention relates to a method for degrading volatile halogenated aliphatic hydrocarbons containing 1 to 3 carbon atoms without producing toxic residues from the degradation. In particular the present invention relates to the use of *Pseudomonas fluorescens* NRRL-B-18296 combined with a carbon source so that halogenated aliphatic hydrocarbon is degraded to non-toxic products (carbon dioxide, water and hydrochloric acid).

(2) Prior Art

Volatile haloaliphatic hydrocarbons are a major source of contamination in underground aquifers since they migrate readily. Most of the hazardous halogenated aliphatic compounds released from industrial, commercial and agricultural sources are chlorinated alkanes and alkenes which contain between one and three carbon atoms. These halogenated aliphatic compounds are exclusively products of human activities and are not produced by nature. The extensive use of these compounds in industrial processes has created a substantial problem in the disposal of waste material and a pollution problem.

The aerobic metabolism of trichloroethylene by Acinetobacter sp. has been reported by Nelson et al (Nelson, M. J., et al., Appl. Environ. Microbiol. 52:383–384 (1986)). This particular bacterium is induced to degrade trichloroethylene through prior growth on phenol (Nelson, M. J., et al., Appl. Environ. Microbiol. 53:949–954 (1987); however this method would be difficult to use in environmental applications since phenol is also a toxic substance. The ability of *Xanthobacter autotrophicus* to metabolize 1,2-dichloroethane and 2-chloroethanol has also been reported (Strotmann, U., et al., Curr. Microbiol. 15:159–163 (1987)).

The volatile haloaliphatic hydrocarbons are resistant to biodegradation in the aerobic subsurface environments such as aquifers, which contributes to their persistence in ground water. Certain anaerobic acetate degrading methanogens are capable of transforming short chained haloaliphatic hydrocarbons; however, they occasionally convert these hydrocarbons into vinyl chloride which was more toxic than the haloaliphatic hydrocarbons (Bouwer, E. J., Appl. Environ. Microbiol 45:1286–1294 (1983)).

It has been estimated that 1,2-chloroethane has an environmental half-life of approximately 50 years (Vogel, T.M., et al., Environ. Sci. Technol. 21:722–736 (1987)). The other volatile halogenated aliphatic hydrocarbons are equally as resistant. The prior art has searched for many years for a Pseudomonas strain which might be effective in degrading these halogenated hydrocarbons.

OBJECTS

It is therefore an object of the present invention to provide a process for degrading volatile halogenated aliphatic hydrocarbons using a bacterium and a carbon source which are harmless in the environment. Further still it is an object of the present invention to provide a method which is simple and economical. These and other object will become increasingly apparent by reference to the following description.

GENERAL DESCRIPTION

The present invention relates to a process for degrading a halogenated aliphatic hydrocarbon containing 1 to 3 carbon atoms which comprises: inoculating a halogenated aliphatic hydrocarbon containing composition with a number of *Pseudomonas fluorescens* NRRL-B-18296 sufficient to produce degradation and incubating the *Pseudomonas fluorescens* in the composition in the presence of oxygen at a temperature which allows the *Pseudomonas fluorescens* NRRL-B-18296 to degrade a substantial portion of the halogenated aliphatic hydrocarbon to carbon dioxide, water and hydrochloric acid. This bacterial strain is unique in that it possesses the ability to degrade these halogenated hydrocarbons in the presence of water, a carbon source, preferably a nitrogen source, and minerals which stimulate growth. *Pseudomonas fluorescens* NRRL-B-18296 is deposited with the Northern Regional Research Laboratory, Peoria, Illinois under the Budapest Treaty.

The strain can be marketed alone or in combination with other strains which degrade other hydrocarbons. It is grown in a suitable growth medium, preferably concentrated, and can be used directly or stored. Preferably the strain is lyophilized or frozen for storage for extended periods of time. The growth media for the strain preferably contains glucose or molasses along with a carbon source, nitrogen source and essential minerals which stimulate the cells for the degradation. All of this is well known to those skilled in the art.

The halogenated hydrocarbons containing 1 to 3 carbon atoms which can be degraded for instance are 1,2-dichloroethane, 1,1,2-trichloroethane, 1,2-dichloropropane, 2,2-dichloropropane, and trichloroethylene. All of these compounds are persistent environmental pollutants.

SPECIFIC DESCRIPTION

The present invention particularly relates to the isolation and use of *Pseudomonas fluorescens* NRRL-B-18296 (internal reference number PFL 12.0) which is able to degrade the halogenated aliphatic hydrocarbons under aerobic conditions in the presence of glucose and upon induction with glucose (or other assimilable sugar). Glucose particularly presents no problems when used in the environment since it is readily degraded in nature.

EXAMPLE 1

A variety of soil and water samples were obtained from a site with a history of industrial 1,2-dichloroethane and 1,2-dichloropropane contamination. The soil and water samples were inoculated into a minimal salts medium (mmo) for liquid culture enrichment and incubated for 72 hours at 25° C. using a method previously described (Stanier, R. Y., et al., J. Gen. Microbiol. 43:159–271 (1966); and Vandenbergh, P.A., et al., Appl. Environ. Microbiol. 42:737–739 (1981). The medium contained glucose as the carbon source (0.2%). After incubation, portions of the enrichments were plated onto several types of media and purified colonies were obtained. A predominant isolate obtained from the enrichment was *P. fluorescens* NRRL-B-18296. This strain was then utilized for the degradation of a variety of chlorinated aliphatic hydrocarbons.

EXAMPLE 2

This Example shows the ability of *Pseudomonas fluorescens* NRRL-B-18296 to degrade various carbon sources grown on minimal media (mmo). The results are shown in Table 1.

TABLE 1

| | Nutritional Properties of *Pseudomonas fluorescens* NRRL-B-18296. | | | | | | |
|---|---|---|---|---|---|---|---|
| | Carbon source[1] | | | | | | |
| Strain | 1,2-di-chloro-ethane | 1,1,2-tri-chloro-ethane | 1,2-di-chloro-propane | 1,3-di-chloro-propane | 2,2-di-chloro-propane | tri-chloro-ethylene | tetra-chloro-ethylene |
| *Pseudomonas fluorescens* NRRL-B-18296 | + | + | + | − | + | + | − |

[1]Incubation was for 72 hours at 25° C. on minimal media (mmo). Volatile carbon sources were supplied in the vapor phase of a sealed container. +, Growth; −, no growth.

Various halogenated 2 and 3 carbon atom sources are degraded.

In Examples 3 to 6, compounds of interest were quantitated using a Perkin-Elmer (model 8500) gas chromatograph equipped with an HS-6 headspace analyzer (Perkin-Elmer, Norwalk, CT). The instrument was fitted with a 6 foot stainless steel Sp2100 column (Supelco, Bellefonte, PA). Carrier gas flow rate (helium) was 20 ml/min. with an isothermal column temperature of 60° C. Injector and detector temperatures were 150° C. and 200° C. respectively.

All sample vials were equilibrated at 80° C. in the headspace analyzer for 10 minutes. Vial pressurization times of 30 seconds and injection times of 6 seconds were both controlled by programmed instrument time functions.

Calibrations were made by the external standard method using the internal data handling capabilities of the instrument. 100 ppm standards were prepared by dispensing 10 ul of the compounds into a serum bottle containing 100.0 g of chilled media analogous to experimental vials. Once the compound was completely dissolved, 2.00 g of the mixture was delivered by syringe to a headspace vial and sealed for subsequent headspace GC analysis.

Analysis of experimental vials was conducted by removing an aliquot by syringe and delivering 2.00 g to a headspace vial. Vials (6 ml) specified for use with the headspace analyzer were sealed using 19 mm TFE/silicone rubber septa and 20 mm crimp top seals (Alltech Associates, Deerfield, IL). A hand operated crimper was utilized.

EXAMPLE 3

This example shows the ability of Pseudomonas fluorescens NRRL-B-18296 to degrade various chloroaliphatic carbon sources in broth minimal media (mmo) broth. The experiments were accomplished in 50 ml of minimal medium (mmo) that was modified. The modified minimal media (mmo) contained the sodium-potassium phosphate buffer at 0.06 M final concentration. The modified (mmo) was supplemented to a final concentration with 0.5% glucose, 0.005% yeast extract, 0.4% potassium nitrate and the volatile chloroaliphatic compound at 100 ppm. The flasks were inoculated with *Pseudomonas fluorescens* NRRL-B-18296 at $10^6$ bacteria/ml. The remaining headspace in the vials was then filled with pure oxygen (approximately 60 ml) and sealed using 19 mm TFE/silicone rubber septa with 20mm crimp top seals. A hand operated crimper was utilized. The sealed vials were then shaken at 350 rpm on a New Brunswick gyrotary shaker (New Brunswick Scientific, Edison, NJ) at 25° C. for 24 hours.

Samples in triplicate (2.00 g) were removed after the 24 hour incubation. The samples were sealed in 6 ml vials and subjected to headspace analysis.

The results depicted in Table 2 demonstrate that *Pseudomonas fluorescens* NRRL-B-18296 was able to utilize a variety of volatile haloaliphatic hydrocarbons containing 2 to 3 chloride atoms per carbon compound.

TABLE 2

| % DEGRADATION OF VARIOUS HALO-ALIPHATIC CARBON SOURCES BY PSEUDOMONAS FLUORESCENS NRRL-B-18296. | | | | | | | |
|---|---|---|---|---|---|---|---|
| | 1,2-di-chloro-propane | 2,2-di-chloro-propane | 1,3-di-chloro-propane | 1,2-di-chloro-ethane | 1,1,1-tri-chloro-ethane | 1,1,2-tri-chloro-ethane | tri-chloro-ethylene | tetra-[1] chloro-ethylene |
| *Pseudomonas fluroescens* NRRL-B-18296 | 3 | 7 | 0 | 10 | 0 | 23 | 2 | 0 |

[1]values reported as percentage amounts of 100 ppm carbon source degraded.

EXAMPLE 4

This example shows the degradation of a mixture of 100 ppm 1,2-dichloroethane and 100 ppm 1,2-dichloropropane in minimal median (mmo) supplemented with 0.1% glucose and 0.4% potassium nitrate using *Pseudomonas fluorescens* NRRL-B-18296. The potassium nitrate provides an assured oxygen source for this strain, since the degradations must be conducted under aerobic conditions.

TABLE 3

| | % Degradation | |
|---|---|---|
| | 1,2-Dichloroethane[1] | 1,2-Dichloropropane[1] |
| *Pseudomonas fluorescens* NRRL-B-18296 | 23.3 | 32.1 |

[1]Experiments were accomplished in 100 ml minimal medium (mmo) supplemented with 0.1% glucose, 100 ppm of 1,2-dichloroethane, 100 ppm of 1,2-dichloropropane, and 0.4% potassium nitrate. The flasks were inoculated with *Pseudomonas fluorescens* NRRL-B-18296 at 10⁶ bacteria/ml, sealed and shaken at 350 rpm on a New Brunswick gyrotary shaker (New Brunswick Scientific, Edison, NJ) at 25° C. for 168 hours. The shaking provides further oxygen to the medium.

The results shown in Table 3 indicated that when *Pseudomonas fluorescens* NRRL-B-18296 was incubated for 168 hours (7 days) in the presence of 0.1% glucose, 100 ppm 1,2-dichloroethane and 100 ppm 1,2 dichloropropane, the degradation rate was 23% and 32%, respectively. Upon extended degradation and supplementing with more glucose, the 1,2-dichloroethane and 1,2-dichloropropane can be substantially completely degraded.

EXAMPLE 5

This example shows the degradation of a mixture of 100 ppm 1,2-dichloroethane and 100 ppm 1,2 dichloropropane in minimal median (mmo) supplemented with 1.0% glucose and 0.4% potassium nitrate using *Pseudomonas fluorescens* NRRL-B-18296. This example uses 10 times as much glucose as in Example 4 and a shorter incubation time.

TABLE 4

|  | % Degradation | |
| --- | --- | --- |
|  | 1,2-Dichloroethane[1] | 1,2-Dichloropropane[1] |
| *Pseudomonas fluoescens* NRRL-B-18296 | 15 | 16 |

[1]Experiments were accomplished in 100 ml minimal medium (mmo) supplemented with 1.0% glucose 100 ppm of 1,2-dichloroethane, 100 ppm of 1,2-dichloropropane, and 0.4% potassium nitrate. The flasks were inoculated with *Pseudomonas fluorescens* NRRL-B-18296 at 10⁶ bacteria/ml, sealed and shaken at 350 rpm on a shaker at 25° C. for 48 hours (2 days).

The results depicted in Table 4 show that when the glucose concentration was increased to 1.0%, the degradative rate of 1,2-dichloroethane and 1,2-dichloropropane was increased, with respect to time. A longer degradation period produced more degradation in the presence of the additional glucose.

EXAMPLE 6

This Example shows the induction of degradation of 1,2-dichloroethane by *Pseudomonas fluorescens* NRRL-B-18296 using a variety of carbon sources. *Pseudomonas fluorescens* NRRL-B-18296 was incubated in 100 ml of mmo containing 0.4% potassium nitrate and supplemented with 20 mM sodium lactate, at 25° C. on a shaker at 350 rpm. After 24 hours of growth, the above culture was utilized as an inoculum for induction studies on a variety of other carbon sources. Sodium lactate is an effective carbon source for this strain although more expensive than glucose.

Individual flasks were supplemented with the following carbon sources at 2mM: ethanol, sodium acetate, glucose, sodium succinate, sodium benzoate, ortho cresol or meta cresol. The induced cultures were grown overnight at 25° C. on a shaker at 350 rpm. After 16 hours, the cells were harvested by centrifugation at 24,000×g at 4° C. for 15 minutes. The pellets were resuspended in sterile distilled water and centrifuged at 24,000×g at 4° C. for 15 minutes. The pellets were resuspended in sterile mmo medium supplemented with 0.4% potassium nitrate until they were at an equivalent cell mass of 10⁶ bacteria/ml based on turbidity at $A_{425}$nm. The cells (0.1 ml) were then inoculated into sterile 6 ml headspace analyzer vials containing 1.9 ml of minimal medium (mmo) supplemented with 0.4% potassium nitrate and 100 ppm of 1,2-dichloroethane. These vials were then sealed using 19 mm TFE/silicone rubber septa and 20 mm crimp top seals (Alltech Associates, Deerfield, IL). The crimped, sealed flasks were then placed on a shaker at 350 rpm and incubated at 25° C. for 24 hours (1 day). After incubation for 24 hours, the vials were analyzed directly on the headspace gas chromatograph. The results are shown in Table 5.

TABLE 5

| Degradation of 1,2-dichloroethane using induced *Pseudomonas fluorescens* NRRL-B-18296 | |
| --- | --- |
| Supplemented Carbon Source | % degradation 1,2-dichloroethane |
| Ethanol | 8.2 |
| Sodium acetate | 5.1 |
| Sodium benzoate | 3.7 |
| Ortho cresol | 1.2 |
| Meta cresol | 5.9 |
| Sodium succinate | 4.4 |
| Glucose | 12.0 |
| None | 0.0 |

The results depicted in Table 4 show that glucose is the best carbon source to induce the degradation of 1,2-dichloroethane for a short time period of degradation.

EXAMPLE 7

This example shows the degradation of 100 ppm of trichloroethylene in minimal medium (mmo) supplemented with 1.0% glucose and 0.4% potassium nitrate using *Pseudomonas fluorescens* NRRL-B-18296.

TABLE 6

|  | % Degradation Trichloroethylene[1] |
| --- | --- |
| *Pseudomonas fluorescens* NRRL-B-18296 | 13.0 |

[1]Experiments were accomplished in 100 ml minimal media (mmo) supplemented with 1.0% glucose, 100 ppm of trichloroethylene, and 0.4% potassium nitrate. The flasks were inoculated with *Pseudomonas fluorescens* NRRL-B-18296 at 10⁶ bacteria/ml, sealed and shaken at 350 rpm on a New Brunswick shaker at 25° C. for 120 hours (5 days).

The results in Table 6 show that *Pseudomonas fluorescens* NRRL-B-18296 was able to degrade 13% of the trichloroethylene in 120 hours (5 days).

Thus as can be seen from Examples 2 to 7 *Pseudomonas fluorescens* NRRL-B-18296 is quite effective in degrading volatile haloaliphatic hydrocarbons which persist in nature. The degradation is performed in the presence of water, either in the environment or in a confined chamber. In the environment the strain plus glucose (or other carbon source) is added to the wet soil or water to accomplish the degradation. Preferably an amount between about 0.01 and 5 percent by weight of the carbon source based upon the weight of water, wet soil or other composition is used. The degradation can be performed under aerobic conditions in the environment and this is easily accomplished without the use of sodium nitrate.

Generally the degradation is accomplished at a temperature between about 15 and 45° C. Along with the carbon source, a nitrogen source (amino acids) or inorganic nitrogen compounds (ammonium chloride) is usually added to insure growth of the *Pseudomonas*

*fluorescens* NRRL-B-18296. The nitrogen source is preferably used in an amount between about 0.001 and 10 percent based upon the weight of water. Preferably between about $10^3$ and $10^{12}$ CFU per ml or gram of the composition are used. Most preferably the cells are concentrated to $10^9$ CFU per ml prior to inoculation into contaminated water or wet soil.

Carbon tetrachloride, dichloromethane and 1,1,1-trichloroethane are not degraded. The reason may be that the strain appears to require a chlorine atom in the number 2 position.

It is intended that the foregoing description be only illustrative of the present invention and that this invention be limited only by the hereinafter appended claims.

We claim:

1. A process for degrading a halogenated aliphatic hydrocarbon containing 1 to 3 carbon atoms which comprises:
   (a) inoculating a halogenated aliphatic hydrocarbon containing composition with a number of *Pseudomonas fluorescens* NRRL-B-18296 sufficient to produce degradation; and
   (b) incubating the Pseudomonas fluorescens in the composition in the presence of oxygen or an oxygen source at a temperature which allows the *Pseudomonas fluorescens* NRRL-B-18296 to degrade a substantial portion of the halogenated aliphatic hydrocarbon to carbon dioxide, water and hydrochloric acid.

2. The process of claim 1 wherein the incubating is at a temperature between about 15° and 45° C.

3. The process of claim 1 wherein the halogenated aliphatic hydrocarbon is selected from the group consisting of 1,2-dichloroethane, 1,2-dichloropropane and trichloroethylene and mixtures thereof.

4. The process of claim 1 wherein a nitrogen source and a carbon source are provided in the composition.

5. The process of claim 1 wherein the number of Pseudomonas fluorescens is between about $10^3$ and $10^{12}$ CFU per ml or gram.

6. The process of claim 1 wherein the cells are grown in a growth medium and concentrated to at least about $10^3$ CFU per ml prior to inoculation and wherein the growth medium contains a carbon source for growth which stimulates the cells of Pseudomonas fluorescens in the presence of the composition.

7. The process of claim 6 wherein the carbon source is glucose or molasses.

8. The process of claim 1 wherein the composition includes a carbon source in an amount which stimulates the growth of the cells of the Pseudomonas fluorescens.

9. The process of claim 8 wherein the carbon source is glucose or molasses.

10. The process of claim 1 wherein the cells are grown in a growth medium and concentrated to at least about $10^3$ CFU per ml prior to inoculation, wherein the growth medium contains a carbon source which stimulates growth of the cells of Pseudomonas fluorescens in the presence of the admixture and wherein the incubating is at a temperature between about 15° and 45° C.

11. The process of claim 10 wherein in addition the composition includes a carbon source in an amount which stimulates the growth of the *Pseudomonas fluorescens* during incubation.

12. The process of claim 11 wherein the carbon source is glucose or molasses.

13. The process of claim 10 wherein between about 0.01 and 5 percent by weight of the carbon source based upon the weight of the composition is provided in the composition.

14. The process of claim 1 wherein the composition includes a carbon source and a nitrogen source in amounts which stimulate the growth of the Pseudomonas fluorescens.

15. The process of claim 14 wherein between about 0.001 and 10 percent by weight of a nitrogen source based upon the wight of the composition is provided in the composition.

16. The process of claim 1 wherein sodium nitrate is provided in the admixture as an oxygen source to supplement the oxygen in the composition.

17. The process of claim 1 which is conducted in the environment.

18. The process of claim 1 which is conducted in a confined chamber.

19. The process of claim 1 wherein the Pseudomonas fluorescens which are inoculated are provided by adding a concentrate of the cells into the composition.

20. The process of claim 1 wherein the Pseudomonas fluorescens which are inoculated are lyophilized.

* * * * *